US006369032B1

(12) United States Patent
Gu et al.

(10) Patent No.: US 6,369,032 B1
(45) Date of Patent: Apr. 9, 2002

(54) METHOD FOR TREATING ALLERGIES

(75) Inventors: Yin Gu, San Diego; Lars Karlsson, La Jolla; Siquan Sun; Robin L. Thurmond, both of San Diego, all of CA (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 0 days.

(21) Appl. No.: 09/946,214

(22) Filed: Sep. 5, 2001

Related U.S. Application Data

(60) Provisional application No. 60/230,407, filed on Sep. 6, 2000.

(51) Int. Cl.$^7$ ...................... A61K 38/00; A61K 31/495; A61K 31/17; A61K 31/16; A61K 31/535
(52) U.S. Cl. .................. 514/12; 514/19; 514/252.1; 514/237.2; 514/588; 514/600
(58) Field of Search .................. 514/12, 19, 252.1, 514/237.2, 588, 600

(56) References Cited

U.S. PATENT DOCUMENTS

| | | | | |
|---|---|---|---|---|
| 5,776,718 A | * | 7/1998 | Palmer et al. | 435/23 |
| 5,830,850 A | * | 11/1998 | Gelb et al. | 514/2 |
| 6,030,946 A | * | 2/2000 | Klaus et al. | 514/12 |

FOREIGN PATENT DOCUMENTS

| WO | WO 99/24460 A2 | * | 5/1999 |
|---|---|---|---|
| WO | WO 99/58153 A1 | | 11/1999 |

OTHER PUBLICATIONS

Eberlein–Konig, et al.; "Immunohistochemical investigation of the cellular infiltrates at the sites of allergoid–induced late–phase cutaneous reactions associated with pollen allergen–specific immunotherapy", Clin. Exp. Allergy (1999) 29:1641–1647.

Gaga, et al.; Eosinophil Activation and T Lymphocyte Infiltration in Allergen–induced Late Phase Skin Reactions and Classical Delayed–Type Hypersensitivity: J. Immunol. (1991) 147:816–822.

Palmer, e al.; "Vinyl Sulfones as Mechanism–Based Cysteine Protease Inhibitors", J. Med. Chem. (1995) 38(17): 3193–3196.

Riese, et al.; "Essential Role for athepsin S in MHC Class II–Associated Invariant Chain Processing and Peptide Loading", Immunity (1996) 4:357–366.

Chapman, H.A. et al.; "Emerging Roles For Cysteine Proteases in Human Biology", Annu. Rev. Physiol. (1997) 59:63–88.

Chapman, H.A. "Endosomal Poteolysis and MHC Class II Function"; curr. Opin. Immunol. (1998) 10:93–102.

Maurer, D. et al.; "Fce Receptor I on Dendritic Cells Delivers IgE–Bound Multivalent Antigens into a Cathepsin S–Dependent Pathway of MHC Class II Presentation" J. Immunol. (1998) 161:2731–2739.

Nakagawa, T. Y. et al.; "Impaired Invariant Chain Degradatiion and Antigen Presentation and Diminished Collagen–Induced Arthritis in cathepsin S Null Mice"; Immunity (1999) 10:207–217.

Nakagawa, T.Y. et al.: "The role of lysosomal proteinases in MHC class II–mediated antigen processing and presentation" Immunological Rev. (1999) 172:121–129.

Riese, R. J. et al.; "Cathepsin S Activity Regulates Antigen Presentation and Immunity"; J. Clin Invest. (1998) 101 (11):2351–2363.

Riese, R.J. et al.; "Cathepsins and Compartmentalization in Antigen Presentation"; Curr. Opin. Immunol. (2000) 12:107–113.

Shi, Guo–Ping, et al.; "Cathepsin S Required for Norman MHC Class II Peptide Loading and Germinal Center Development"; Immunity (1999) 10:197–206.

Villadangos, J. A. et al.; "Degradation of Mouse Invariant Chain: Roles of Cathepsins S and D and the Influence of Major Histocompatibility Complex Polymorphism" J. Exp. Med. (1997) 186(4):549–560.

Villadangos, J. A. et al.; "Proteases Involved in MHC Class II Antigen Presentation" Immunological Rev. (1999)172:109–120.

Villadangos, J.A. et al.; "Proteolysis in MHC Class II Antigen Presentation: Who's in Charge?"; Immunity (2000) 12:233–239.

* cited by examiner

Primary Examiner—Raymond Henley, III

(57) ABSTRACT

Use of cathepsin S inhibitors for the treatment of an allergic condition, in particular an atopic allergic condition, more specifically for the treatment of hay fever, asthma, atopic dermatitis or a food allergy.

18 Claims, 2 Drawing Sheets

1A.

1B.

METHOD FOR TREATING ALLERGIES

This Application claims benefit from U.S. Provisional Application No. 60/230,407, filed Sep. 6, 2000.

FIELD OF THE INVENTION

The present invention relates to the use of cathepsin S inhibitors for the treatment of an allergic condition, in particular an atopic allergic condition.

BACKGROUND OF THE INVENTION

Atopic allergies afflict at least 20% of populations in developed countries and comprise a wide range of IgE-mediated diseases such as hay fever, asthma, atopic dermatitis, and food allergies. Exposure of an allergic subject to relevant allergens cross-links allergen specific IgE bound to mast cells, triggering degranulation and release of proinflammatory mediators, such as histamine and eicosanoids, which cause the weal-and-flare response on a skin test. Characteristically, this early response is followed by a prolonged late reaction in which inflammatory cells, particularly eosinophils and activated TH-2 CD4 T cells, are recruited to the site of allergen exposure. Inflammatory cytokines such as IL-4 and IL-5, both produced by TH-2 cells, are important for IgE production by B cells and for eosinophilia, respectively. Immunotherapies targeting CD4 T cells have been shown to be effective in reducing the production of IgE, the activation of proinflammatory cells, and the release of inflammatory mediators.

Current allergy therapies targeting CD4 T cells have met with mixed success. Desensitization with allergen extracts or vaccines is effective for many allergens, such as the Hymenoptera insect sting which can induce life-threatening allergic reactions. The mechanism may be either induction of T cell tolerance or the conversion of TH-2 to TH-1. However, such treatment requires a long-term treatment regime, frequent doctor visits and prior stabilization by other medications, and is associated with a certain morbidity rate and rare deaths. Alternatively, immunosuppressive drugs such as steroids which effectively stabilize ongoing allergy responses, are often associated with severe side effects.

The activation of CD4 T cells is a major factor in the initiation and maintenance of the allergic response. Allergens are taken up by specialized antigen presenting cells (APCs) such as dendritic cells and B cells. Protein allergens pass through the endosomal or lysosomal system where they are degraded by different proteases. These peptide fragments are bound by the MHC class II molecules which, at the cell surface, are heterotrimeric complexes consisting of two transmembrane glycoprotein chains ($\alpha$ and $\beta$) that form a binding scaffold for the third component, a peptide of 11–20 amino acids. The antigen-MHC class II molecule complex is recognized by CD4 T cells and leads to the activation of the T cell. Activated T cells in turn activate several other components of the immune system, such as B cells and macrophages, that are crucial for the body's response to pathogens, but also lead to the symptoms of allergies.

Class II molecules, like other transmembrane proteins, are translocated into the endoplasmic reticulum (ER) after synthesis, where they associate with a third protein, the invariant chain (Ii). The invariant chain molecule is a type II transmembrane protein that serves as a class II-specific chaperone, promoting the exit of class II-Ii complexes from the ER and preventing class II molecules from binding to peptides and unfolded proteins in the ER and in the secretory pathway. A targeting motif in the cytoplasmic tail of Ii directs the class II-Ii complexes from the secretory pathway into the endosomal system.

Before the MHC class II molecules can present antigen the Ii must be removed by a series of proteases that break down Ii. The resultant Ii peptide fragments, called class II-associated invariant chain peptides (CLIP), occupy the peptide binding groove of the class II molecule, and in most cases are not spontaneously released. The CLIP protects the class II binding pocket from collapsing both during intracellular transport and after Ii degradation in the endosomal system. Binding of antigenic peptides generated from endocytosed proteins requires an empty, and yet open binding site. The CLIP therefore must be released while the open binding site is stabilized to allow the binding of other peptides. Human Leukocyte Antigen—DM ('HLA-DM') mediates both of these functions, thus promoting the binding of antigenic peptides. After acquiring peptides, the class II molecules are transported to the cell surface via routes that are largely unknown.

In view of the above, inhibition of invariant chain proteolysis will prevent removal of Ii from the class II binding pocket, which in turn will specifically block antigen binding to the MHC class II molecule.

Cathepsin S ('CatS') is a cysteine protease expressed in lymphatic tissues. CatS mediates invariant chain proteolysis, which is a prerequisite for peptide loading of MHC class II molecules (Riese et al. (1996) Immunity 4:357). CatS has 50–60% homology with cathepsins L and K, but differs from them in that it has a broad pH optimum that extends to alkaline pH. CatS modulates antigen presentation in animal models, and inhibitors are effective in an asthma model (Riese et al. (1998) J. Clin. Invest. 101:2351). Mice deficient in cathepsin S have an impaired ability to present exogenous proteins by professional antigen presenting cells (Nakagawa et al. (1999) Immunity 10:207; Shi et al. (1999) Immunity 10:197).

Compounds that inhibit the proteolytic activity of human cathepsin S are expected to find utility in the treatment of chronic autoimmune diseases including, but not limited to, lupus and rheumatoid arthritis; and have potential utility in modulating the immune response to tissue transplantation. Methods of modulating autoimmunity with an agent that modulates cathepsin S activity, e.g., proteolysis of the Ii chain, as well as methods of treating a subject having an autoimmune disorder, methods of evaluating a treatment for its ability to modulate an immune response are described in WO 99/58153.

SUMMARY OF THE INVENTION

The present invention features the use of cathepsin S inhibitors to treat allergic conditions, including but not limited to atopic allergies. Examples of an allergic condition include hay fever, asthma, atopic dermatitis and food allergies. Allergens include dust, pollen, mold, and pet dander or pet hair.

In one aspect, the invention provides a method for treating a subject suffering from an allergic condition, in particular an atopic allergic condition, said method comprising administering to said subject a therapeutically effective amount of a pharmaceutical composition comprising a cathepsin S inhibitor.

In another aspect, the invention provides a method for treating a subject suffering from an IgE-mediated allergic condition, in particular an atopic allergic condition, said method comprising administering to said subject a therapeutically effective amount of a pharmaceutical composition comprising a cathepsin S inhibitor.

A third aspect of the invention provides the use, or the use for the manufacture of a medicament, of a cathepsin S inhibitor for treating an allergic condition, more in particular for treating IgE-mediated allergic conditions, still more in particular treating hay fever, asthma, atopic dermatitis or food allergies. The invention also features anti-allergic pharmaceutical compositions comprising as active ingredient an effective amount of a cathepsin S inhibitor, and a pharmaceutically acceptable carrier. The active ingredient can be formulated in any manner suitable for the particular allergic condition, including aerosol, oral and topical formulations and time-release formulations.

Cathepsin S inhibitors are known in the art; alternatively, they can be identified using methods known in the art, such as the Cathepsin S inhibition assay described in Example 1 below.

Additional features and advantages of the invention will become apparent from the detailed description and examples below, and the appended claims.

BRIEF DESCRIPTION OF THE FIGURES

FIG. 1A: Dilution curve for purified PBMC from an allergy donor were cultured with titrated doses of allergen extracts prepared from Derp and Der for seven days. Proliferation of T cells was scored by measuring $^3$H-thymidine incorporation for 18 h at the end of culture. Bottom panel, FIG. 1B: Effect of titrated doses of LHVS on proliferative responses of T cells to dust mite extracts.

FIG. 2A: Dilution curve for purified PBMC from an allergy donor were cultured with titrated doses of allergen extracts prepared from Ragweed short and Ragweed giant for seven days. Proliferation of T cells was scored by measuring $^3$H-thymidine incorporation for 18 h at the end of culture. Bottom panel, FIG. 2B: Effect of titrated doses of LHVS on proliferative responses of T cells to ragweed extracts.

DETAILED DESCRIPTION OF THE INVENTION

Figure 1:
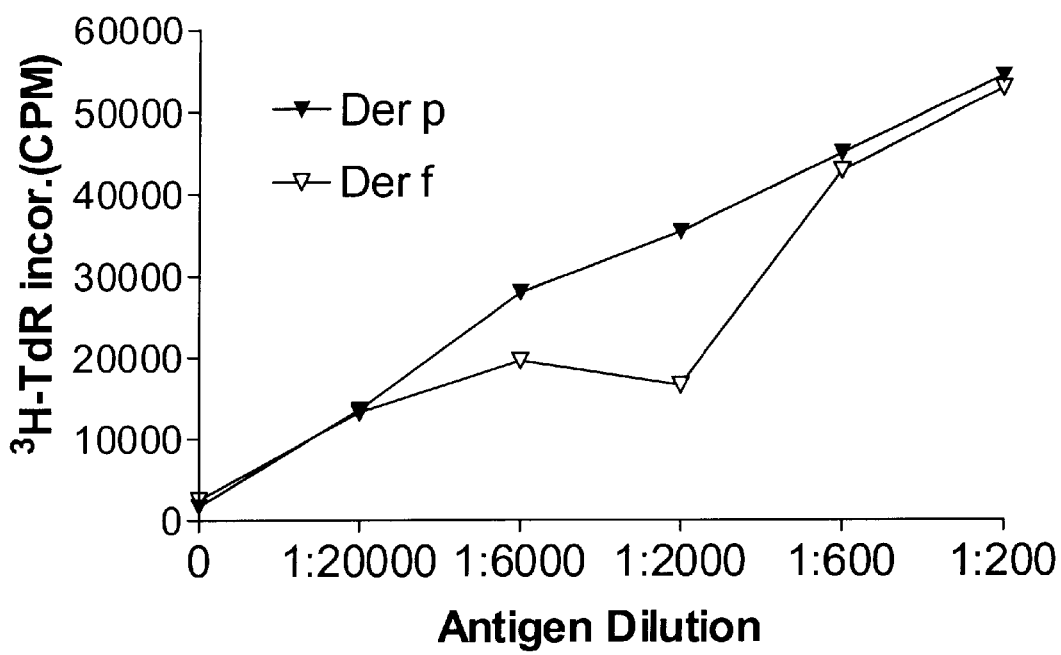
FIG. 1 shows the inhibition of human T cell proliferative responses to two species of dust mites, Derp and Derf. Top panel.
Figure 1:
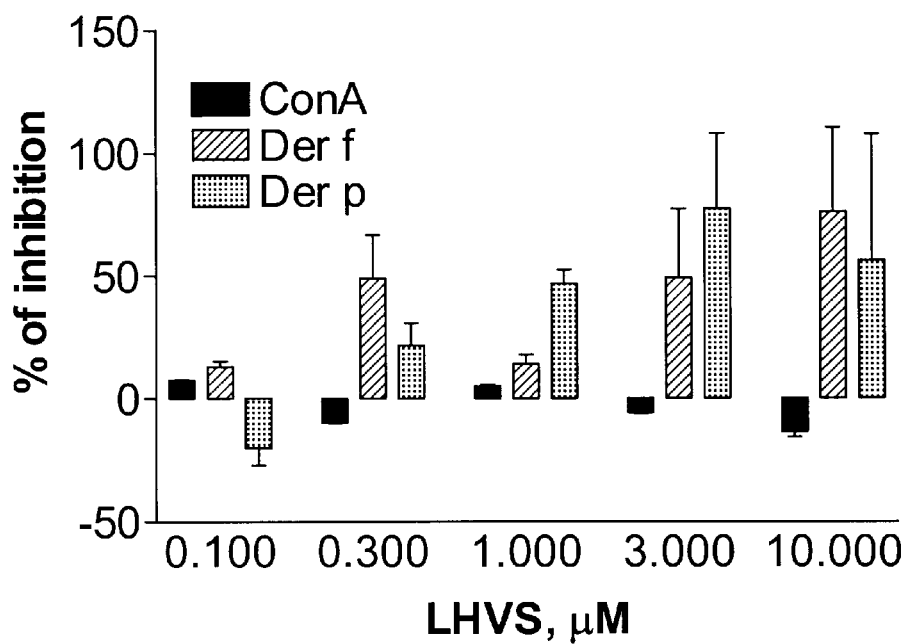

A target of the present invention was to determine whether the presentation of particular antigens in a human system is affected by the inhibition of cathepsin S. According to the invention, it now has been found that inhibitors of cathepsin S block the presentation of several crude allergen extracts in a human ex vivo assay, thereby supporting the use of cathepsin S inhibitors for the treatment of such allergic conditions.

Blocking Ii degradation should decrease antigen presentation to CD4 T cells and disrupt the normal immune response. A cathepsin S inhibitor should specifically affect the activation of CD4 T cells, thus limiting the extent of concomitant immunosuppression, an undesirable side effect of corticosteroid therapy.

By using cathepsin S inhibitors according to the methods of the present invention, the immunological component of the allergic reaction can be blocked to varying degrees, with the advantage over current therapies of being more selective, having fewer or reduced side effects, or both. The present invention is based, in part, on the finding that cathepsin S inhibitors can block the presentation of crude allergen extracts in a human ex vivo assay. This ex vivo system closely mimics the process that occurs in the whole body wherein antigens enter the blood stream, and are presented by antigen presenting cells, which in turn activate CD4 T cells. In the case of treating a subject, the inhibitor or a metabolite thereof would also be present in the blood as in the ex vivo assay.

A. TERMS

The following terms are defined below and by their usage throughout this disclosure.

"Alkyl" includes optionally substituted straight chain and branched hydrocarbons with at least one hydrogen removed to form a radical group. Alkyl groups include methyl, ethyl, propyl, isopropyl, butyl, isobutyl, t-butyl, 1-methylpropyl, pentyl, isopentyl, sec-pentyl, hexyl, heptyl, octyl, and so on. Alkyl includes cycloalkyl, such as cyclopropyl, cyclobutyl, cyclopentyl, and cyclohexyl.

"Alkenyl" includes optionally substituted straight chain and branched hydrocarbon radicals as above with at least one carbon-carbon double bond ($sp^2$). Alkenyls include ethenyl (or vinyl), prop-1-enyl, prop-2-enyl (or allyl), isopropenyl (or 1-methylvinyl), but-1-enyl, but-2-enyl, butadienyls, pentenyls, hexa-2,4-dienyl, and so on. Hydrocarbon radicals having a mixture of double bonds and triple bonds, such as 2-penten-4-ynyl, are grouped as alkynyls herein. Alkenyl includes cycloalkenyl. Cis and trans or (E) and (Z) forms are included within the invention.

"Alkynyl" includes optionally substituted straight chain and branched hydrocarbon radicals as above with at least one carbon-carbon triple bond (sp). Alkynyls include ethynyl, propynyls, butynyls, and pentynyls. Hydrocarbon radicals having a mixture of double bonds and triple bonds, such as 2-penten-4-ynyl, are grouped as alkynyls herein. Alkynyl does not include cycloalkynyl.

"Alkoxy" includes an optionally substituted straight chain or branched alkyl group with a terminal oxygen linking the alkyl group to the rest of the molecule. Alkoxy includes methoxy, ethoxy, propoxy, isopropoxy, butoxy, t-butoxy, pentoxy and so on. "Aminoalkyl", "thioalkyl", and "sulfonylalkyl" are analogous to alkoxy, replacing the terminal oxygen atom of alkoxy with, respectively, NH (or NR), S, and $SO_2$. Heteroalkyl includes alkoxy, aminoalkyl, thioalkyl, and so on.

"Aryl" includes phenyl, naphthyl, biphenylyl, tetrahydronaphthyl, and so on, any of which may be optionally substituted. Aryl also includes arylalkyl groups such as benzyl, phenethyl, and phenylpropyl. Aryl includes a ring system containing an optionally substituted 6-membered carbocyclic aromatic ring, said system may be bicyclic, bridge, and/or fused. The system may include rings that are aromatic, or partially or completely saturated. Examples of ring systems include indenyl, pentalenyl, 1-4-dihydronaphthyl, indanyl, benzimidazolyl, benzothiophenyl, indolyl, benzofuranyl, isoquinolinyl, and so on.

"Heterocyclyl" includes optionally substituted aromatic and nonaromatic rings having carbon atoms and at least one heteroatom (O, S, N) or heteroatom moiety ($SO_2$, CO, CONH, COO) in the ring. Unless otherwise indicated, a heterocyclic radical may have a valence connecting it to the rest of the molecule through a carbon atom, such as 3-furyl or 2-imidazolyl, or through a heteroatom, such as N-piperidyl or 1-pyrazolyl. Preferably a monocyclic heterocyclyl has between 4 and 7 ring atoms, or between 5 and 6 ring atoms; there may be between 1 and 5 heteroatoms or heteroatom moieties in the ring, and preferably between 1 and 3. A heterocyclyl may be saturated, unsaturated, aromatic (e.g., heteroaryl), nonaromatic, or fused.

Heterocyclyl also includes fused, e.g., bicyclic, rings, such as those optionally condensed with an optionally substituted carbocyclic or heterocyclic five- or six-membered aromatic ring. For example, "heteroaryl" includes an optionally substituted six-membered heteroaromatic ring containing 1, 2 or 3 nitrogen atoms condensed with an optionally substituted five- or six-membered carbocyclic or heterocyclic aromatic ring. Said heterocyclic five- or six-membered aromatic ring condensed with the said five- or six-membered aromatic ring may contain 1, 2 or 3 nitrogen atoms where it is a six-membered ring, or 1, 2 or 3 heteroatoms selected from oxygen, nitrogen and sulfur where it is a five-membered ring.

Examples of heterocyclyls include thiazoylyl, furyl, pyranyl, isobenzofuranyl, pyrrolyl, imidazolyl, pyrazolyl, isothiazolyl, isoxazolyl, pyridyl, pyrazinyl, pyrimidinyl, pyridazinyl, indolizinyl, isoindolyl, indolyl, indazolyl, purinyl, quinolyl, furazanyl, pyrrolidinyl, pyrrolinyl, imdazolidinyl, imidazolinyl, pyrazolidinyl, pyrazolinyl, piperidyl, piperazinyl, indolinyl, and morpholinyl. For example, preferred heterocyclyls or heterocyclic radicals include morpholinyl, piperazinyl, pyrrolidinyl, pyridyl, cyclohexylimino, cycloheptylimino,and more preferably, piperidyl.

Examples illustrating heteroaryl are thienyl, furanyl, pyrrolyl, imidazolyl, oxazolyl, thiazolyl, benzothienyl, benzofuranyl, benzimidazolyl, benzoxazolyl, benzothiazolyl.

"Acyl" refers to a carbonyl moiety attached to either a hydrogen atom (i.e., a formyl group) or to an optionally substituted alkyl or alkenyl chain, or heterocyclyl.

"Halo" or "halogen" includes fluoro, chloro, bromo, and iodo, and preferably chloro or bromo as a substituent.

"Alkanediyl" or "alkylene" represents straight or branched chain optionally substituted bivalent alkane radicals such as, for example, methylene, ethylene, propylene, butylene, pentylene or hexylene.

"Alkenediyl" represents, analogous to the above, straight or branched chain optionally substituted bivalent alkene radicals such as, for example, propenylene, butenylene, pentenylene or hexenylene. In such radicals, the carbon atom linking a nitrogen preferably should not be unsaturated.

"Aroyl" refers to a carbonyl moiety attached to an optionally substituted aryl or heteroaryl group, wherein aryl and heteroaryl have the definitions provided above. In particular, benzoyl is phenylcarbonyl.

As defined herein, two radicals, together with the atom(s) to which they are attached may form an optionally substituted 4- to 7-, 5- to 7-, or a 5- to 6-membered ring carbocyclic or heterocyclic ring, which ring may be saturated, unsaturated or aromatic. Said rings may be as defined above in the Summary of the Invention section. Particular examples of such rings are as follows in the next section.

"Pharmaceutically acceptable salts, esters, and amides" include carboxylate salts (e.g., $C$, alkyl, cycloalkyl, aryl, heteroaryl, or non-aromatic heterocyclic) amino acid addition salts, esters, and amides which are within a reasonable benefit/risk ratio, pharmacologically effective and suitable for contact with the tissues of patients without undue toxicity, irritation, or allergic response. Representative salts include hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate, and laurylsulfonate. These may include alkali metal and alkali earth cations such as sodium, potassium, calcium, and magnesium, as well as non-toxic ammonium, quaternary ammonium, and amine cations such as tetramethyl ammonium, methylamine, trimethylamine, and ethylamine. See example, S.M. Berge, et al., "Pharmaceutical Salts," J. Pharm. Sci., 1977, 66:1–19 which is incorporated herein by reference. Representative pharmaceutically acceptable amides of the invention include those derived from ammonia, primary $C_{1-6}$alkyl amines and secondary di($C_{1-6}$alkyl) amines. Secondary amines include 5- or 6-membered heterocyclic or heteroaromatic ring moieties containing at least one nitrogen atom and optionally between 1 and 2 additional heteroatoms. Preferred amides are derived from ammonia, $C_{1-3}$alkyl primary amines, and di ($C_{1-2}$alkyl)amines. Representative pharmaceutically acceptable esters of the invention include $C_{1-7}$alkyl, $C_{5-7}$cycloalkyl, phenyl, and phenyl($C_{1-6}$)alkyl esters. Preferred esters include methyl esters.

"Patient" or"subject" includes mammals such as humans and animals (dogs, cats, horses, rats, rabbits, mice, non-human primates) in need of observation, experiment, treatment or prevention in connection with the relevant disease or condition. Preferably, the patient or subject is a human.

"Composition" includes a product comprising the specified ingredients in the specified amounts as well as any product which results directly or indirectly from combinations of the specified ingredients in the specified amounts.

"Therapeutically effective amount" or "effective amount" means that amount of active compound or pharmaceutical agent that elicits the biological or medicinal response in a tissue system, animal or human that is being sought by a researcher, veterinarian, medical doctor or other clinician, which includes alleviation of the symptoms of the allergic disease or disorder being treated.

Concerning the various radicals in this disclosure and in the claims, three general remarks are made. The first remark concerns valency. As with all hydrocarbon radicals, whether saturated, unsaturated or aromatic, and whether or not cyclic, straight chain, or branched, and also similarly with all heterocyclic radicals, each radical includes substituted radicals of that type and monovalent, bivalent, and multivalent radicals as indicated by the context of the claims. The context will indicate that the substituent is an alkylene or hydrocarbon radical with at least two hydrogen atoms removed (bivalent) or more hydrogen atoms removed (multivalent). An example of a bivalent radical linking two parts of the molecule is G in formula (I) which links two rings.

Second, radicals or structure fragments as defined herein are understood to include substituted radicals or structure fragments. Hydrocarbyls include monovalent radicals containing carbon and hydrogen such as alkyl, alkenyl, alkynyl, cycloalkyl, and cycloalkenyl (whether aromatic or unsaturated), as well as corresponding divalent radicals such as alkylene, alkenylene, phenylene, and so on. Heterocarbyls include monovalent and divalent radicals containing carbon, hydrogen, and at least one heteroatom. Examples of monovalent heterocarbyls include acyl, acyloxy, alkoxyacyl, heterocyclyl, heteroaryl, aroyl, benzoyl, dialkylamino, hydroxyalkyl, and so on. Using "alkyl" as an example, "alkyl" should be understood to include substituted alkyl having one or more substitutions, such as between 1 and 5, 1 and 3, or 2 and 4 substituents. The substituents may be the same (dihydroxy, dimethyl), similar (chlorofluoro), or different (chlorobenzyl- or aminomethyl-substituted). Examples of substituted alkyl include haloalkyl (such as fluoromethyl, chloromethyl, difluoromethyl, perchloromethyl, 2-bromoethyl, perfluoromethyl, and 3-iodocyclopentyl), hydroxyalkyl (such as hydroxymethyl, hydroxyethyl, 2-hydroxypropyl, aminoalkyl (such as aminomethyl, 2-aminoethyl, 3-aminopropyl, and 2-aminopropyl), nitroalkyl, alkylalkyl, and so on. A di($C_{1-6}$alkyl)amino group includes independently selected alkyl groups, to form, for example, methylpropylamino and isopropylmethylamino, in addition dialkylamino groups having two of the same alkyl group such as dimethyl amino or diethylamino.

Third, only stable compounds are intended. For example, where there is an NR'R" group, and R can be an alkenyl group, the double bond is at least one carbon removed from the nitrogen to avoid enamine formation. Similarly, where a dashed line is an optional $sp^2$ bond, if it is absent, the appropriate hydrogen atom(s) is(are) included.

Compounds of the invention are further described in the next section.

B. COMPOUNDS

The invention features the treatment of an allergic condition using one or more cathepsin S inhibitors as described in the Summary section.

Suitable cathepsin S inhibiting compounds for use in the methods according to the present invention are those disclosed in the art or found to be CatS inhibitors by methods known in the art (see Example 1 below). Examples of suitable compounds for use in the methods of the invention include (a) the group of dipeptidyl nitrites disclosed in WO-99/24460 by Altmann, et al. (Novartis); (b) the group of dipeptidyl vinyl sulfones disclosed by Palmer, et al. in U.S. Pat No. 5,976,858, assigned to Arris (now Axys), as cysteine protease inhibitors, including cathepsin S inhibitors, and in particular, morpholinurea-leucine-homo-phenylalanine-vinylsulfonephenyl ('LHVS'), also referred to as 4-morpholinecarboxamide, N-[(1S)-3-methyl-1-[[[(1S,2E)-1-(2-phenylethyl)-3-(phenylsulfonyl)-2-propenyl]amino]carbonyl]butyl]-; (c) the group of peptidyl sulfonamides disclosed by Palmer, et al. in U.S. Pat. No. 5,776,718, also assigned to Arris/Axys, (d) the compounds disclosed by Klaus, et al. in U.S. Pat. No. 6,030,946 as cysteine protease inhibitors, including cathepsin S, inhibitors. The former is assigned to Arris, now Axys, the latter to Axys; and (e) the group of cathepsin S inhibitors described in WO 99/58153. All five above-cited patents or patent applications provide how to make the disclosed compounds and how to test them for protease and/or CatS inhibitory activity. These patents or patent applications are incorporated entirely herein by reference.

Related Compounds

The invention provides the disclosed compounds and closely related, pharmaceutically acceptable forms of the disclosed compounds, such as salts, esters, amides, acids, hydrates or solvated forms thereof; masked or protected forms; and racemic mixtures, or enantiomerically or optically pure forms. Related compounds also include compounds of the invention that have been modified to be detectable, e.g., isotopically labelled with $^{18}F$ for use as a probe in positron emission tomography (PET) or single-photon emission computed tomography (SPECT).

The invention also includes disclosed compounds having one or more functional groups (e.g., hydroxyl, amino, or carboxyl) masked by a protecting group. See, e.g., Greene and Wuts, *Protective Groups in Organic Synthesis*, $3^{rd}$ ed., (1999) John Wiley & Sons, NY. Some of these masked or protected compounds are pharmaceutically acceptable; others will be useful as intermediates. Synthetic intermediates and processes disclosed herein, and minor modifications thereof, are also within the scope of the invention.

HYDROXYL PROTECTING GROUPS

Protection for the hydroxyl group includes methyl ethers, substituted methyl ethers, substituted ethyl ethers, substitute benzyl ethers, and silyl ethers.

Substituted Methyl Ethers

Examples of substituted methyl ethers include methyoxymethyl, methylthiomethyl, t-butylthiomethyl, (phenyldimethylsilyl)methoxymethyl, benzyloxymethyl, p-methoxybenzyloxymethyl, (4-methoxyphenoxy)methyl, guaiacolmethyl, t-butoxymethyl, 4-pentenyloxymethyl, siloxymethyl, 2-methoxyethoxymethyl, 2,2,2-trichloroethoxymethyl, bis(2-chloroethoxy)methyl, 2-(trimethylsilyl)ethoxymethyl, tetrahydropyranyl, 3-bromotetrahydropyranyl, tetrahydrothiopyranyl, 1-methoxycyclohexyl, 4-methoxytetrahydropyranyl, 4-methoxytetrahydrothiopyranyl, 4-methoxytetrahydrothiopyranyl S,S-dioxido, 1-[(2-chloro-4-methyl)phenyl]-4-methoxypiperidin-4-yl, 1,4-dioxan-2-yl, tetrahydrofuranyl, tetrahydrothiofuranyl and 2,3,3a,4,5,6,7,7a-octahydro-7,8,8-trimethyl-4,7-methanobenzofuran-2-yl.

Substituted Ethyl Ethers

Examples of substituted ethyl ethers include 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, and benzyl.

Substituted Benzyl Ethers

Examples of substituted benzyl ethers include p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2- and 4-picolyl, 3-methyl-2-picolyl N-oxide, diphenylmethyl, p, p'-dinitrobenzhydryl, 5-dibenzosuberyl, triphenylmethyl, α-naphthyidiphenylmethyl, p-methoxyphenyidiphenylmethyl, di(p-methoxyphenyl)phenylmethyl, tri(p-methoxyphenyl)methyl, 4-(4'-bromophenacyloxy)phenyldiphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(Imidazol-1-ylmethyl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, and benzisothiazolyl S,S-dioxido.

Silyl Ethers

Examples of silyl ethers include trimethylsilyl, triethylsilyl, triisopropylsilyl, dimethylisopropylsilyl, diethylisopropylsilyl, dimethylthexylsilyl, t-butyldimethylsilyl, t-butyidiphenylsilyl, tribenzylsilyl, tri-p-xylylsilyl, triphenylsilyl, diphenylmethylsilyl, and t-butylmethoxyphenylsilyl.

Esters

In addition to ethers, a hydroxyl group may be protected as an ester. Examples of esters include formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, p-P-phenylacetate, 3-phenylpropionate, 4-oxopentanoate(levulinate), 4,4-(ethylenedithio)pentanoate, pivaloate, adamantoate, crotonate, 4-methoxycrotonate, benzoate, p-phenylbenzoate, 2,4,6-trimethyl benzo ate(mesito ate)

Carbonates

Examples of carbonate protecting groups include methyl, 9-fluorenylmethyl, ethyl, 2,2,2-trichloroethyl, 2-(trimethylsilyl)ethyl, 2-(phenylsulfonyl)ethyl, 2-(triphenylphosphonio)ethyl, isobutyl, vinyl, allyl, p-nitrophenyl, benzyl, p-methoxybenzyl, 3,4-dimethoxybenzyl, o-nitrobenzyl, p-nitrobenzyl, S-benzyl thiocarbonate, 4-ethoxy-1-naphthyl, and methyl dithiocarbonate.

Assisted Cleavage

Examples of assisted cleavage include 2-iodobenzoate, 4-azidobutyrate, 4-nitro-4-methylpentanoate, o-(dibromomethyl)benzoate, 2-formylbenzenesulfonate, 2-(methylthiomethoxy)ethyl carbonate, 4-(methylthiomethoxy)butyrate, and 2-(methylthiomethoxymethyl)benzoate.

Miscellaneous Esters

Examples of miscellaneous esters include 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate (tigloate), o-(methoxycarbonyl)benzoate, p-P-benzoate, α-naphthoate, nitrate, alkyl N,N,N',N'-tetramethylphosphorodiamidate, N-phenylcarbamate, borate, dimethylphosphinothioyl, and 2,4-dinitrophenylsulfenate.

Sulfonates

Examples of sulfonates include sulfate, methanesulfonate (mesylate), benzylsulfonate, and tosylate.

AMINO PROTECTING GROUPS

Protection for the amino group includes carbamates, amides, and special—NH protective groups.

Examples of carbamates include methyl and ethyl carbamates, substituted ethyl carbamates, assisted cleavage carbamates, photolytic cleavage carbamates, urea-type derivatives, and miscellaneous carbamates.

Carbamates

Examples of methyl and ethyl carbamates include methyl and ethyl, 9-fluorenylmethyl, 9-(2-sulfo)fluorenylmethyl, 9-(2,7-dibromo)fluorenylmethyl, 2,7-di-t-butyl-[9-(10,10-dioxo-10,10,10,10-tetrahydrothioxanthyl)]methyl, and 4-methoxyphenacyl.

Substituted Ethyl

Examples of substituted ethyl carbamates include 2,2,2-trichloroethyl, 2- trimethylsilylethyl, 2-phenylethyl, 1-(1-adamantyl)-1-methylethyl, 1,1-dimethyl-2-haloethyl, 1,1-dimethyl-2,2-dibromoethyl, 1,1-dimethyl-2,2,2-trichloroethyl, 1-methyl-1-(4-biphenylyl)ethyl, 1-(3,5-di-t-butylphenyl)-1-methylethyl, 2-(2'- and 4'-pyridyl)ethyl, 2-(N,N-dicyclohexylcarboxamido)ethyl, t-butyl, 1-adamantyl, vinyl, allyl, 1-isopropylallyl, cinnamyl, 4-nitrocinnamyl, 8-quinolyl, N-hydroxypiperidinyl, alkyldithio, benzyl, p-methoxybenzyl, p-nitrobenzyl, p-bromobenzyl, p-chlorobenzyl, 2,4-dichlorobenzyl, 4-methylsulfinylbenzyl, 9-anthrylmethyl and diphenylmethyl.

Assisted Cleavage

Examples of assisted cleavage include 2-methylthioethyl, 2-methylsulfonylethyl, 2-(p-toluenesulfonyl)ethyl, [2-(1,3-dithianyl)]methyl, 4-methylthiophenyl, 2,4-dimethylthiophenyl, 2-phosphonioethyl, 2-triphenylphosphonioisopropyl, 1,1-dimethyl-2-cyanoethyl, m-chloro-p-acyloxybenzyl, p-(dihydroxyboryl)benzyl, 5-benzisoxazolylmethyl, and 2-(trifluoromethyl)-6-chromonylmethyl.

Photolytic Cleavage

Examples of photolytic cleavage include m-nitrophenyl, 3,5-dimethoxybenzyl, o-nitrobenzyl, 3,4-dimethoxy-6-nitrobenzyl, and phenyl(o-nitrophenyl)methyl.

Urea-Type Derivatives

Examples of urea-type derivatives include phenothiazinyl-(10)-carbonyl derivative, N'-p-toluenesulfonylaminocarbonyl, and N'-phenylaminothiocarbonyl.

Miscellaneous Carbamates

Examples of miscellaneous carbamates include t-amyl, S-benzyl thiocarbamate, p-cyanobenzyl, cyclobutyl, cyclohexyl, cyclopentyl, cyclopropylmethyl, p-decyloxybenzyl, diisopropylmethyl, 2,2-dimethoxycarbonylvinyl, o-(N,N-dimethylcarboxamido) benzyl, 1,1-dimethyl-3-(N,N-dimethylcarboxamido)propyl, 1,1-dimethylpropynyl, di(2-pyridyl)methyl, 2-furanylmethyl, 2-iodoethyl, isobornyl, isobutyl, isonicotinyl, p-(p'-methoxyphenylazo)benzyl, 1-methylcyclobutyl, 1-methylcyclohexyl, 1-methyl-1-cyclopropylmethyl, 1-methyl-1-(3,5-dimethoxyphenyl) ethyl, 1-methyl-1-(p-phenylazophenyl)ethyl, 1-methyl-1-phenylethyl, 1-methyl-1-(4-pyridyl)ethyl, phenyl, p-(phenylazo)benzyl, 2,4,6-tri-t-butylphenyl, 4-(trimethylammonium)benzyl, and 2,4,6-trimethylbenzyl.

Examples of Amides Include:

Amides

N-formyl, N-acetyl, N-chloroacetyl, N-trichloroacetyl, N-trifluoroacetyl, N-phenylacetyl, N-3-phenylpropionyl, N-picolinoyl, N-3-pyridylcarboxamide, N-benzoylphenylalanyl derivative, N-benzoyl, N-p-phenylbenzoyl.

Assisted Cleavage

N-o-nitrophenylacetyl, N-o-nitrophenoxyacetyl, N-acetoacetyl, (N'-dithiobenzyloxycarbonylamino)acetyl, N-3-(p-hydroxyphenyl)propionyl, N-3-(o-nitrophenyl) propionyl, N-2-methyl-2-(o-nitrophenoxy)propionyl, N-2-methyl-2-(o-phenylazophenoxy)propionyl, N-4-chlorobutyryl, N-3-methyl-3-nitrobutyryl, N-o-nitrocinnamoyl, N-acetylmethionine derivative, N-o-nitrobenzoyl, N-o-(benzoyloxymethyl)benzoyl, and 4,5-diphenyl-3-oxazolin-2-one.

Cyclic Imide Derivatives

N-phthalimide, N-dithiasuccinoyl, N-2,3-diphenylmaleoyl, N-2,5-dimethylpyrrolyl, N-1,1,4,4-tetramethyldisilylazacyclopentane adduct, 5-substituted 1,3-dimethyl-1,3,5-triazacyclohexan-2-one, 5-substituted 1,3-dibenzyl-1,3,5-triazacyclohexan-2-one, and 1-substituted 3,5-dinitro-4-pyridonyl.

SPECIAL—NH PROTECTIVE GROUPS

Examples of special NH protective groups include N-Alkyl and N-Aryl Amines

N-methyl, N-allyl, N-[2-(trimethylsilyl)ethoxy]methyl, N-3-acetoxypropyl, N-(1-isopropyl-4-nitro-2-oxo-3-pyrrolin-3-yl), quaternary ammonium salts, N-benzyl, N-di(4-methoxyphenyl)methyl, N-5-dibenzosuberyl, N-triphenylmethyl, N-(4-methoxyphenyl)diphenylmethyl, N-9-phenylfluorenyl, N-2,7-dichloro-9-fluorenylmethylene, N-ferrocenylmethyl, and N-2-picolylamine N'-oxide.

Imine Derivatives

N-1,1-dimethylthiomethylene, N-benzylidene, N-p-methoxybenzylidene, N-diphenylmethylene, N-[(2-pyridyl)mesityl]methylene, and N-(N',N'-dimethylaminomethylene).

PROTECTION FOR THE CARBONYL GROUP

Acyclic Acetals and Ketals

Examples of acyclic acetals and ketals include dimethyl, bis(2,2,2-trichloroethyl), dibenzyl, bis(2-nitrobenzyl) and diacetyl.

Cyclic Acetals and Ketals

Examples of cyclic acetals and ketals include 1,3-dioxanes, 5-methylene-1,3-dioxane, 5,5-dibromo-1,3-dioxane, 5-(2-pyridyl)-1,3-dioxane, 1,3-dioxolanes, 4-bromomethyl-1,3-dioxolane, 4-(3-butenyl)-1,3-dioxolane, 4-phenyl-1,3-dioxolane, 4-(2-nitrophenyl)-1,3-dioxolane, 4,5-dimethoxymethyl-1,3-dioxolane, O,O'-phenylenedioxy and 1,5-dihydro-3H-2,4-benzodioxepin.

Acyclic Dithio Acetals and Ketals

Examples of acyclic dithio acetals and ketals include S,S'-dimethyl, S,S'-diethyl, S,S'-dipropyl, S,S'-dibutyl, S,S'-dipentyl, S,S'-diphenyl, S,S'-dibenzyl and S,S'-diacetyl.

Cyclic Dithio Acetals and Ketals

Examples of cyclic dithio acetals and ketals include 1,3-dithiane, 1,3-dithiolane and 1,5-dihydro-3H-2,4-benzodithiepin.

Acyclic Monothio Acetals and Ketals

Examples of acyclic monothio acetals and ketals include O-trimethylsilyl-S-alkyl, O-methyl-S-alkyl or -S-phenyl and O-methyl-S-2-(methylthio)ethyl.

Cyclic Monothio Acetals and Ketals

Examples of cyclic monothio acetals and ketals include 1,3-oxathiolanes.

MISCELLANEOUS DERIVATIVES

O-Substituted Cyanohydrins

Examples of O-substituted cyanohydrins include O-acetyl, O-trimethylsilyl, O-1-ethoxyethyl and O-tetrahydropyranyl.

Substituted Hydrazones

Examples of substituted hydrazones include N,N-dimethyl and 2,4-dinitrophenyl.

Oxime Derivatives

Examples of oxime derivatives include O-methyl, O-benzyl and O-phenylthiomethyl.

Imines

Substituted Methylene Derivatives, Cyclic Derivatives

Examples of substituted methylene and cyclic derivatives include oxazolidines, 1-methyl-2-(1'-hydroxyalkyl)imidazoles, N,N'-dimethylimidazolidines, 2,3-dihydro-1,3-benzothiazoles, diethylamine adducts, and methylaluminum bis(2,6-di-t-butyl-4-methylphenoxide)(MAD)complex.

PROTECTION FOR THE CARBOXYL GROUP

Esters

Substituted Methyl Esters

Examples of substituted methyl esters include 9-fluorenylmethyl, methoxymethyl, methylthiomethyl, tetrahydropyranyl, tetrahydrofuranyl, methoxyethoxymethyl, 2-(trimethylsilyl)ethoxymethyl, benzyloxymethyl, phenacyl, p-bromophenacyl, α-methylphenacyl, p-methoxyphenacyl, carboxamidomethyl, and N-phthalimidomethyl.

2-Substituted Ethyl Esters

Examples of 2-substituted ethyl esters include 2,2,2-trichloroethyl, 2-haloethyl, ω-chloroalkyl, 2-(trimethylsilyl)ethyl, 2-methylthioethyl, 1,3-dithianyl-2-methyl, 2-(p-nitrophenylsulfenyl)ethyl, 2-(p-toluenesulfonyl)ethyl, 2-(2'-pyridyl)ethyl, 2-(diphenylphosphino)ethyl, 1-methyl-1-phenylethyl, t-butyl, cyclopentyl, cyclohexyl, allyl, 3-buten-1-yl, 4-(trimethylsilyl)-2-buten-1-yl, cinnamyl, α-methylcinnamyl, phenyl, p-(methylmercapto)phenyl and benzyl.

Substituted Benzyl Esters

Examples of substituted benzyl esters include triphenylmethyl, diphenylmethyl, bis(o-nitrophenyl)methyl, 9-anthrylmethyl, 2-(9,10-dioxo)anthrylmethyl, 5-dibenzosuberyl, 1-pyrenylmethyl, 2-(trifluoromethyl)-6-chromylmethyl, 2,4,6-trimethylbenzyl, p-bromobenzyl, o-nitrobenzyl, p-nitrobenzyl, p-methoxybenzyl, 2,6-dimethoxybenzyl, 4-(methylsulfinyl)benzyl, 4-sulfobenzyl, piperonyl, 4-picolyl and p-P-benzyl.

Silyl Esters

Examples of silyl esters include trimethylsilyl, triethylsilyl, t-butyidimethylsilyl, i-propyidimethylsilyl, phenyldimethylsilyl and di-t-butylmethylsilyl.

Activated Esters

Examples of activated esters include thiols.

Miscellaneous Derivatives

Examples of miscellaneous derivatives include oxazoles, 2-alkyl-1,3-oxazolines, 4-alkyl-5-oxo-1,3-oxazolidines, 5-alkyl-4-oxo-1,3-dioxolanes, ortho esters, phenyl group and pentaaminocobalt(III) complex.

Stannyl Esters

Examples of stannyl esters include triethylstannyl and tri-n-butylstannyl.

AMIDES AND HYDRAZIDES

Amides

Examples of amides include N,N-dimethyl, pyrrolidinyl, piperidinyl, 5,6-dihydrophenanthridinyl, o-nitroanilides, N-7-nitroindolyl, N-8-Nitro-1,2,3,4-tetrahydroquinolyl, and p-P-benzenesulfonamides.

Hydrazides

Examples of hydrazides include N-phenyl and N,N'-diisopropyl hydrazides.

C. FORMULATION AND ADMINISTRATION

The present compounds inhibit the proteolytic activity of human cathepsin S and therefore are useful as a medicine especially in methods for treating patients suffering from allergic disorders or conditions which are modulated or regulated by the inhibition of cathepsin S activity.

The invention features a method for treating a subject with an allergic condition mediated by cathepsin S, said method comprising administering to the subject a therapeutically effective amount of a pharmaceutical composition comprising a compound of the invention. The invention also provides a method for inhibiting cathepsin S activity in a subject, wherein the method comprises administering to the subject a therapeutically effective amount of a pharmaceutical composition comprising a compound of the invention In view of their inhibitory effect on the proteolytic activity of human cathepsin S the compounds of the present invention may be formulated into various pharmaceutical forms for administration purposes. To prepare these pharmaceutical compositions, an effective amount of a particular compound, in base or acid addition salt form, as the active ingredient is intimately mixed with a pharmaceutically acceptable carrier.

A carrier may take a wide variety of forms depending on the form of preparation desired for administration. These pharmaceutical compositions are desirably in unitary dosage form suitable, preferably, for oral administration or parenteral injection. For example, in preparing the compositions in oral dosage form, any of the usual pharmaceutical media may be employed. These include water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. In view of their ease in administration, tablets and capsules represent the most advantageous oral dosage unit form, in which case solid pharmaceutical carriers are generally employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not cause a significant deleterious effect to the skin. Such additives may facilitate the administration to the skin and/or may be helpful for preparing the desired compositions. These compositions may be administered in various ways, e.g., as a transdermal patch, as a spot-on, as an ointment. Acid addition salts of the compounds of formula I, due to their increased water solubility over the corresponding base form, are more suitable in the preparation of aqueous compositions.

It is especially advantageous to formulate the aforementioned pharmaceutical compositions in dosage unit form for ease of administration and uniformity of dosage. Dosage unit form as used in the specification herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

Pharmaceutically acceptable acid addition salts include the therapeutically active non-toxic acid addition salt forms which the disclosed compounds are able to form. The latter can conveniently be obtained by treating the base form with an appropriate acid. Appropriate acids comprise, for example, inorganic acids such as hydrohalic acids, e.g. hydrochloric or hydrobromic acid; sulfuric; nitric; phosphoric and the like acids; or organic acids such as, for example, acetic, propanoic, hydroxyacetic, lactic, pyruvic, oxalic, malonic, succinic, maleic, fumaric, malic, tartaric, citric, methanesulfonic, ethanesulfonic, benzenesulfonic, p-toluenesulfonic, cyclamic, salicylic, p-aminosalicylic, pamoic and the like acids. The term addition salt also comprises the solvates which the disclosed componds, as well as the salts thereof, are able to form. Such solvates are for example hydrates, alcoholates and the like. Conversely the salt form can be converted by treatment with alkali into the free base form.

Stereoisomeric forms defines all the possible isomeric forms which the compounds of formula (I) may possess. Unless otherwise mentioned or indicated, the chemical designation of compounds denotes the mixture of all possible stereochemically isomeric forms, said mixtures containing all diastereomers and enantiomers of the basic molecular structure. More in particular, sterogenic centers may have the (R)- or (S)-configuration; substituents on bivalent cyclic saturated radicals may have either the cis- or trans-configuration. The invention encompasses stereochemically isomeric forms including diastereoisomers, as well as mixtures thereof in any proportion of the disclosed compounds. The disclosed compounds may also exist in their tautomeric forms. Such forms although not explicitly indicated in the above and following formulae are intended to be included within the scope of the present invention.

Those of skill in the treatment of disorders or conditions mediated by the cathepsin S enzyme could easily determine the effective daily amount from the test results presented hereinafter and other information. In general it is contemplated that a therapeutically effective dose would be from 0.001 mg/kg to 5 mg/kg body weight, more preferably from 0.01 mg/kg to 0.5 mg/kg body weight. It may be appropriate to administer the therapeutically effective dose as two, three, four or more sub-doses at appropriate intervals throughout the day. Said sub-doses may be formulated as unit dosage forms, for example, containing 0.05 mg to 250 mg, and in particular 0.5 to 50 mg of active ingredient per unit dosage form. Examples include 2 mg, 4 mg, 7 mg, 10 mg, 15 mg, 25 mg, and 35 mg dosage forms. Compounds of the invention may also be prepared in time-release or subcutaneous or transdermal patch formulations. Disclosed compound may also be formulated as a spray or other topical or inhalable formulations.

The exact dosage and frequency of administration depends on the particular compound of formula (I) used, the particular condition being treated, the severity of the condition being treated, the age, weight and general physical condition of the particular patient as well as other medication the patient may be taking, as is well known to those skilled in the art. Furthermore, it is evident that said effective daily amount may be lowered or increased depending on the response of the treated patient and/or depending on the evaluation of the physician prescribing the compounds of the instant invention. The effective daily amount ranges mentioned herein are therefore only guidelines.

The next section includes detailed information relating to the use of the disclosed compounds.

D. EXAMPLES

Example 1

Cathepsin S Inhibition Assay

Recombinant human cathepsin S (CatS) is expressed in the baculovirus system and purified in one step with a thiopropyl-sepharose column. 10-L yielded ~700 mg of CatS and N-terminal sequencing confirmed identity. The assay is run in 100 mM sodium acetate pH 5.0 containing 1 mM DTT and 100 mM NaCl. The substrate for the assay is (Aedens)EKARVLAEM(Dabcyl)K-amide The $K_m$ for the substrate is around 5 $\mu$M but the presence of substrate inhibition makes kinetic analysis difficult. With 20 $\mu$M substrate the assay rate is linear over the range of 1–8 ng CatS in 100 $\mu$l reaction. Using 2 ng/well of CatS, the production of product is linear and yields ~7-fold signal after 20 min with only 20% loss of substrate. Primary assays are run by quenching the reaction after 20 min with 0.1% SDS and then measuring the fluorescence. For other assays, measurements are taken every min for 20 min. The rate is calculated from the slope of the increase and the percent inhibition is calculated from this.

Example 2

Ex Vivo Inhibition by Cathepsin S Inhibitors of the Allergenic Response

The following assay demonstrates that cathepsin S inhibitors block the response of human T cells to crude allergen extracts.

Materials and Methods

Reagents. Glycerinated crude allergen extracts of house dust mites (*Dermataphagoides pteronyssinus, Dermataphagoides farinae*) and ragweed [*Ambrosia trifida* (giant), *Ambrosia artemisiifolia* (short)] were purchased from Hollister-Stier Laboratories (Minneapolis, Minn.). Concanavalin A (ConA) was purchased from Calbiochem (La Jolla, Calif.).

Donors. All allergic donors were prescreened for their specific allergies using RAST tests. The HLA class II haplotypes of these donors were determined using PCR.

Cell culture. Human peripheral blood mononuclear cells (PBMC) were purified from blood of allergic donors using Ficoll-Hypaque gradient followed by washes with phosphate buffered saline (PBS). PBMC were cultured in triplicate or duplicate at $0.5-1.0 \times 10^6$ cells/well with titrated doses of allergen extracts, in the presence or absence of a known cathepsin S inhibitor, LHVS (morpholinurea-leucine-homo-phenylalanine-vinylsulfonephenyl) (Palmer et al. (1995), J. Med. Chem. 38:3193 and Riese et al. (1996), Immunity 4:357). Serial diluted stock solutions of LHVS were first made in 100% DMSO and then diluted 1:15 in 40% Hydroxypropynyl cyclodextrin (HPCD). Three microliters of LHVS in HPCD was added into PBMC cultures (200 µL/well). After 6 days of culture, 1 µCi/well of $^3$H-thymidine (TdR) was added. Eighteen hours later, cells were harvested using a Filtermate Harvester (Packard) and counted for $^3$H-TdR incorporation on Topcount (Packard).

Inhibition of T cell proliferative responses to house dust mites.

About 10% of most populations are allergic to house dust mites (HDM) of the genus Dermatophagoides with *Dermatophagoides pteronyssinus* (Der p) and *D. farinae* (Der f) being the two major species present in varying proportions in most countries. The major clinical manifestations are asthma and perennial rhinitis.

Effect of cathepsin S inhibition on activation of HDM allergen-specific CD4 T cells was tested in an ex vivo human T cell-proliferation assay. Culturing PBMC with crude extracts from either Der p or Der f, resulted in strong proliferation (FIG. 1A). This proliferation consisted primarily of allergen-specific CD4 T cells. When cathepsin S activity was blocked by a specific cathepsin S inhibitor, LHVS (cf. Riese et al. (1996) Immunity 4:357) the proliferation was strongly inhibited (FIG. 1B). Inhibition by LHVS was specific for responses induced by HDM extracts since T cell proliferative responses induced by ConA, a pan-T cell mitogen, were not affected. Furthermore, this inhibition was observed for all four HDM-allergic donors tested regardless of the different HLA class II haplotypes (DR4; DR7, 15; DR11, 15; and DR4, 11).

This system is very similar to an in vivo situation. The allergic subject would be exposed to a crude mixture of allergens that would lead to the proliferation of T cells and an allergic response. The observation of inhibition of CD4 T cell activation by a cathepsin S inhibitor shows that such inhibitors can be effective in treating a generalized population of patients allergic to house dust mites.

Inhibition of T cell proliferative responses to ragweed

About 10% of population in US are allergic to ragweed pollen, making it one of the most important allergens in terms of clinical diseases. Allergens from pollens are a common precipitant of rhinitis and asthma in this population.

Figure 2:
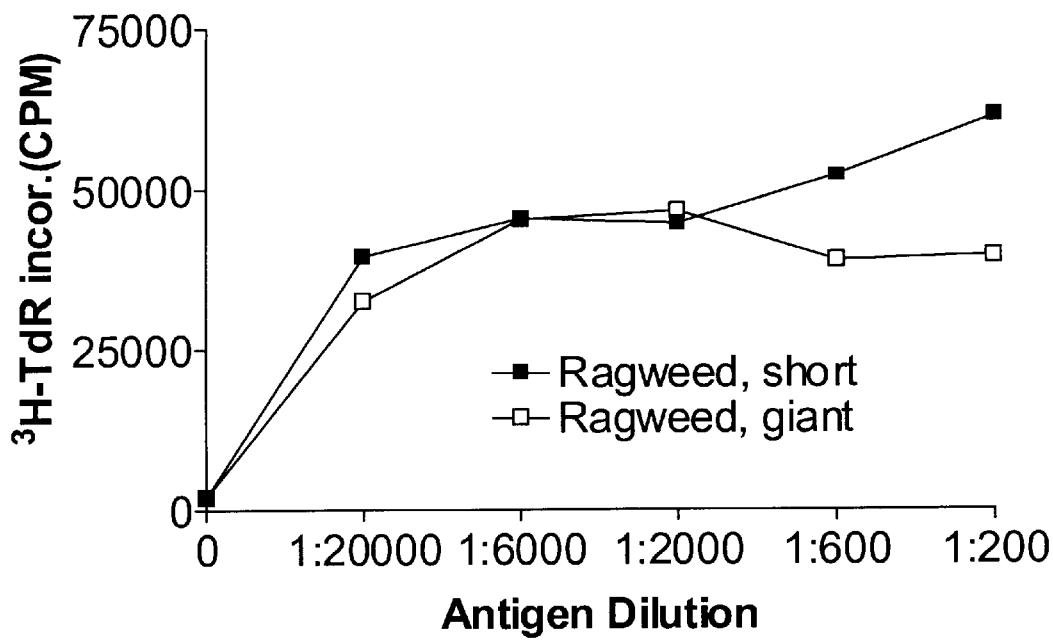
FIG. 2 is shows the inhibition of human T cell proliferative responses to ragweeds but not ConA by LHVS. Top panel.
Figure 2:
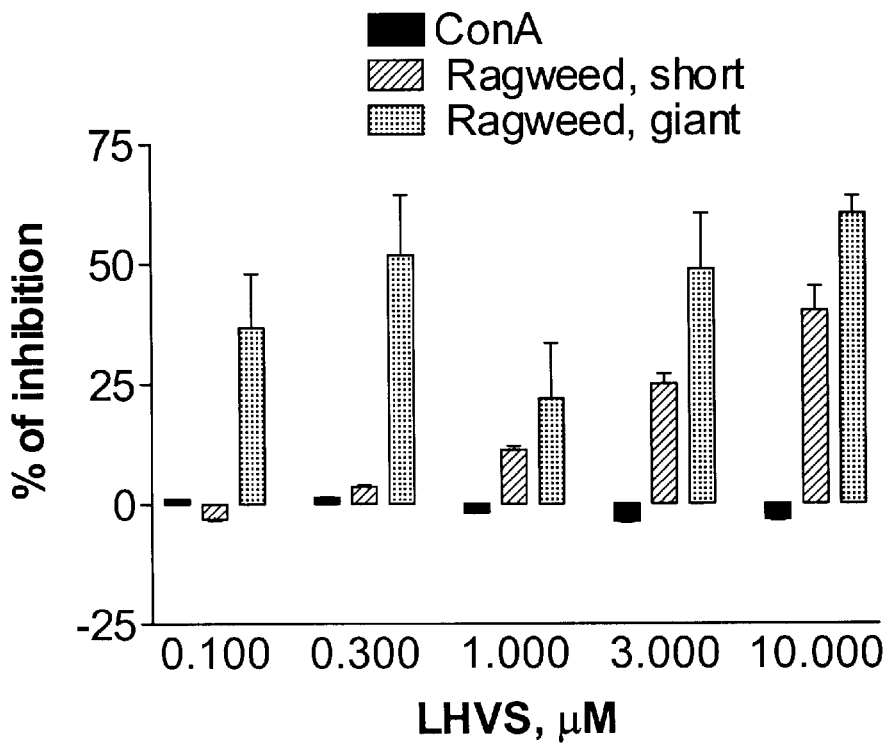

The effect of cathepsin S inhibition on activation of ragweed allergen-specific CD4 T cells was tested in an ex vivo human T cell-proliferation assay. Culturing PBMC with crude extracts from both short and giant ragweed resulted in strong proliferation (FIG. 2A). This proliferation consisted mainly of allergen-specific CD4 T cells. When cathepsin S activity was blocked by a specific cathepsin S inhibitor, LHVS (cf. Riese et al. (1996) Immunity 4:357) the proliferation was strongly inhibited (FIG. 2B). Inhibition by LHVS was specific for responses induced by ragweed since T cell proliferative responses induced by ConA, a pan-T cell mitogen, were not affected. Furthermore, this inhibition was observed for the two ragweed-allergic donors tested regardless of the different HLA class II haplotypes (DR7, 15 and DR4, 11).

This system is very similar to an in vivo situation. The allergic subject would be exposed to a crude mixture of allergens that would lead to the proliferation of T cells and an allergic response. The observation of inhibition of CD4 T cell activation by a cathepsin S inhibitor shows that such inhibitors can be effective in treating a generalized population of patients allergic to ragweed.

Example 3

Monitoring Cathepsin S Inhibition in Human Blood

The effect of in vivo administration of cathepsin S inhibitors, in a clinical trial setting, can be monitored by measuring accumulation of an intermediate degradation product of invariant chain (Ii), i.e. the p10Ii fragment, in blood of dosed subjects. After administration of a cathepsin inhibitor for a certain period of time, for example, 0.01 to 50 mg/kg/day to result in a blood concentration of preferably 1 nM–10 µM for 16–30 h, blood is drawn and white blood cells are purified, e.g. either by lysis of red blood cells or by a Ficoll-Hypaque gradient centrifugation. Whole cell lysates of WBC are then made and analyzed by either a Western blot assay or an ELISA assay. For the Western blot assay, cell lysates are first resolved on SDS-PAGE gels. After transferring to nitrocellulose membranes, Ii and its intermediate degradation products, including the p10Ii, can be detected using a mouse mAb against Ii, e.g. Pin1.1, or rabbit polyclonal antibodies or a mouse monoclonal antibody specific for the p10Ii fragment or against the entire p10Ii fragment. For ELISA assay, a pair of antibodies against Ii, including Pin1.1, and a rabbit polyclonal antibody against C-terminal of p10Ii, can be used. The same assay can also be applied to monitor the effect of cathepsin S inhibitors in vivo in animal studies, for example in monkeys, dogs, pigs, rabbits, guinea pigs, and rodents.

In the present example PBMC from human blood were incubated with the cathepsin S inhibitor, LHVS (morpholinurea-leucine-homo-phenylalanine-vinylsulfonephenyl, also referred to as 4-morpholinecarboxamide, N-[(1S)-3-methyl-1-[[[(1S,2E)-1-(2-phenylethyl)-3-(phenylsulfonyl)-2-5 propenyl]amino]carbonyl]butyl]-. This compound has been described in U.S. Pat. No. 5,976,858 and in Palmer et al. (1995) J. Med. Chem.

38:3193 and Riese et al. (1996) Immunity 4:357. After incubation for 24 h the samples were run using standard SDS-PAGE protocols, transferred to nitrocellulose membranes and probed with an antibody that recognizes the invariant chain including the p10Ii fragment. In the presence of LHVS the p10Ii fragment was seen, representing a block in the degradation of Ii due to inhibition of cathepsin S.

Example 4

Monitoring in Vivo Inhibition of Allergenic Response by Cathepsin S Inhibitors

To demonstrate the efficacy of cathepsin S inhibitors for suppressing allergic responses in vivo, allergic volunteers are dosed with cathepsin S inhibitors to levels where invariant chain degradation is inhibited. Allergens are deposited subcutaneously, and the size of the cutaneous react ions are determined at 15 min, 6 h and 24 h. Skin biopsies are performed at 24 h. The immediate weal and flare response is not mediated by a T cell response and is not expected to be influenced by cathepsin S inhibitors, while the late phase induration (noticeable at 6 hours, more pronounced at 24 hours) is characterized by activation and infiltration of CD4 T cells (as well as of eosinophils) and should be inhibited by administration of inhibitors of cathepsin S. The skin biopsies are used to determine the cellular composition in the induration, and cathepsin S treated subjects are expected to have fewer activated CD4 T cells present than placebo-treated subjects.

References for these procedures are provided in Eberlein-Konig et al. (1999) Clin. Exp. Allergy 29:1641–1647 and in Gaga et al. (1991) J. Immunol. 147:816–822.

As controls for the experiment, prednisone and cyclosporine A will be used. Prednisone will inhibit both the immediate and the late phase responses, while cyclosporin A will inhibit only the late phase response.

E. Other Embodiments

The features and advantages of the invention are apparent to one of ordinary skill in the art. Based on this disclosure, including the summary, detailed description, background, examples, and claims, one of ordinary skill in the art will be able to make modifications and adaptations to various conditions and usages. These other embodiments are also within the scope of the invention.

What is claimed is:

1. A method of treating a subject suffering from an allergic condition, said method comprising administering to said subject a therapeutically effective amount of a pharmaceutical composition comprising a cathepsin S inhibitor.

2. A method according to claim 1, wherein the allergic condition is an atopic IgE-mediated allergic condition.

3. A method according to claim 1, wherein the allergic condition is selected from hay fever, asthma, atopic dermatitis, and a food allergy.

4. A method of claim 1, wherein said cathepsin S inhibitor is a compound of formula:

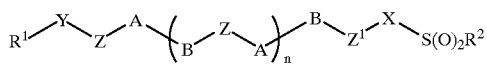

in which: n is 0 to 13;

A—B represents a linkage selected from —C(O)NR$^3$—, —CH$_2$NR$^3$—, —C(O)CH$_2$— and —NR$^3$C(O)—, wherein R$^3$ is hydrogen or as defined below;

X represents a bond, methylene or the linkage —CH$_2$CH(R$^4$)—, wherein R$^4$ is hydrogen, alkyl or arylalkyl;

Y is —CH(R$^5$)— or —N(R$^5$)—, wherein R$^5$ is hydrogen or as defined below;

Z is —(CH$_2$)$_2$—, —C(R$^6$)(R$^7$)— or —N(R$^7$)—, wherein R$_6$ is hydrogen or methyl and R$^7$ is as defined below;

Z$^1$ is —(CH$_2$)$_2$—, —C(R$^6$)(R$^8$)— or —N(R$^8$)—, wherein R$^6$ is hydrogen or methyl and R$^8$ is as defined below; R$^1$ is hydrogen, alkyloxycarbonylalkanoyl, alkyloxycarbonyl, alkanoyl (optionally substituted with a radical selected from carboxy, alkyloxycarbonyl and heterocycloalkylalkanoylamino), cycloalkylcarbonyl, heterocycloalkylcarbonyl (optionally substituted with a radical selected from hydroxy, alkyl, alkanoyl, alkyloxycarbonyl, arylalkyloxycarbonyl and heterocycloalkylcarbonyl), arylalkyloxycarbonyl, carbamoyl, alkylcarbamoyl, dialkylcarbamoyl, arylcarbamoyl, arylalkylcarbamoyl, arylalkanoyl, aroyl, alkylsulfonyl, dialkylaminosulfonyl, arylsulfonyl or heteroarylsulfonyl;

R$^7$ and R$^8$ are independently hydrogen, alkyl (optionally substituted with a radical selected from hydroxy, amino, alkylamino, dialkylamino, uriedo, mercapto, alkylthio, carboxy, carbamoyl, alkylcarbamoyl, dialkylcarbamoyl, alkylsulfonyl and guanidino, or a protected derivative thereof, cycloalkyl, cycloalkylalkyl, heteroaryl, heteroarylalkyl, a group selected from aryl and arylalkyl (which group is optionally substituted at its aryl ring with one to three radicals selected from hydroxy, amino, guanidino, halo, optionally halo-substituted alkyl, alkyloxy and aryl, or a protected derivative thereof) or together with an adjacent R$^3$ or R$^5$ forms a divalent radical selected from (C$_{3-4}$)methylene and 1,2-phenylenedimethylene (which radical is optionally substituted with hydroxy, or a protected derivative thereof, or oxo); and R$^2$ is hydrogen, alkyl (optionally substituted with one or more radicals selected from amino, halo, hydroxy, alkyloxy, nitro, alkylsulfonyl and arylsulfonyl, or a protected derivative thereof, cycloalkyl, cycloalkylalkyl or a group selected from aryl and arylalkyl (which group is optionally substituted at its aryl ring with one to two radicals selected from amino, guanidino, halo, hydroxy, optionally halo-substituted alkyl, alkyloxy, nitro, alkylsulfonyl and arylsulfonyl, or a protected derivative thereof; or a pharmaceutically acceptable salt, isomer or mixture of isomers thereof.

5. The method of claim 4, wherein said cathepsin S inhibitor is a compound wherein Z is —C(R$^6$)(R$^7$)—; n is 0; R$^3$, R$^5$ and R$^8$ are each hydrogen; R$^1$ is hydrogen, tert-butoxycarbonyl, benzyloxycarbonyl, biotinylaminohexanoyl, benzoyl, 1-piperiziny-carbonyl, 4-methyl-1-piperazinylcarbonyl or 4-morpholinylcarbonyl; R$^8$ is butyl, 2-phenylethyl or 2-methylsulfonylethyl; R$^2$ is phenyl, 1-naphthyl or 2-phenylethyl; and R$^7$ is (C$_{1-5}$)alkyl, 2-methylsulfonylethyl, optionally substituted benzyl, 1-naphthylmethyl, 2-naphthylmethyl, 3-pyridinylmethyl or 2-methylsulfonylethyl.

6. The method of claim 5, wherein said cathepsin S inhibitor is a compound wherein R$^1$ is 1-piperizinylcarbonyl, 4-methyl-1-piperazincarbonyl or 4-morpholinylcarbonyl; R$^8$ is 2-phenylethyl; R$^2$ is phenyl or naphth-2-yl; and R$^7$ is optionally substituted benzyl, 1-naphthylmethyl or 2-naphthylmethyl.

7. A method of claim 1, wherein said cathepsin S inhibitor is a compound of formula:

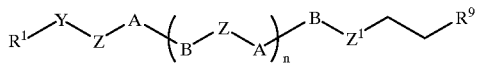

in which:

n is 0 to 13;

A—B represents a linkage selected from —C(O)NR$^3$—, —CH$_2$NR$^3$—, —C(O)CH$_2$— and —NR$^3$C(O)—, wherein R$^3$ is hydrogen or as defined below;

Y is —CH(R$^5$)— or —N(R$^5$)—, wherein R$^5$ is hydrogen or as defined below;

Z is —(CH$_2$)$_2$—, —C(R$^6$)(R$^7$)— or —N(R$^7$)—, wherein R$^6$ is hydrogen or methyl and R$^7$ is as defined below;

Z$^1$ is —(CH$_2$)$_2$—, —C(R$^6$)(R$^8$)— or —N(R$^8$)—, wherein R$^6$ is hydrogen or methyl and R$^8$ is as defined below;

R$^1$ is hydrogen, alkyloxycarbonylalkanoyl, alkyloxycarbonyl, alkanoyl (optionally substituted with a radical selected from carboxy, alkyloxycarbonyl and heterocycloalkylalkanoylamino), cycloalkylcarbonyl, heterocycloalkylcarbonyl (optionally substituted with a radical selected from hydroxy, alkyl, alkanoyl, alkyloxycarbonyl, arylalkyloxycarbonyl and heterocycloalkylcarbonyl), arylalkyloxycarbonyl, carbamoyl, alkylcarbamoyl, dialkylcarbamoyl, arylcarbamoyl, arylalkylcarbamoyl, arylalkanoyl, aroyl, alkylsulfonyl, dialkylaminosulfonyl, arylsulfonyl or heteroarylsulfonyl;

R$^7$ and R$^8$ are independently hydrogen, alkyl (optionally substituted with a radical selected from hydroxy, amino, alkylamino, dialkylamino, uriedo, mercapto, alkylthio, carboxy, carbamoyl, alkylcarbamoyl, dialkylcarbamoyl, alkylsulfonyl and guanidino, or a protected derivative thereof), cycloalkyl, cycloalkylalkyl, heteroaryl, heteroarylalkyl, a group selected from aryl and arylalkyl (which group is optionally substituted at its aryl ring with one to three radicals selected from hydroxy, amino, guanidino, halo, optionally halo-substituted alkyl, alkyloxy and aryl, or a protected derivative thereof) or together with an adjacent R$^3$ or R$^5$ forms a divalent radical selected from a divalent radical selected from (C$_{3-4}$)methylene and 1,2-phenylenedimethylene (which radical is optionally substituted with hydroxy, or a protected derivative thereof, or oxo); and R$^9$ is cyano, —C(O)OR$^{10}$, —P(O)(OR$^{10}$)$_2$, —S(O)(NR$^{10}$)R$^{10}$, C(O)R$^{11}$, —S(O)R$^{11}$, —C(O)NR$^{12}$ R$^{13}$, —S(O)$_2$NR$^{12}$R$^{13}$; —C(O)NHR$^{14}$ or —S(O)$_2$NHR$^{14}$, wherein each R$^{10}$ is independently hydrogen, alkyl (optionally substituted with one or more radicals selected from amino, halo, hydroxy, alkyloxy, nitro, alkylsulfonyl and arylsulfonyl, or a protected derivative thereof), cycloalkyl, cycloalkylalkyl or a group selected from aryl and arylalkyl (which group is optionally substituted at its aryl ring with one to two radicals selected from amino, halo, hydroxy, optionally halosubstituted alkyl, alkyloxy, nitro, alkylsulfonyl and arylsulfonyl, or a protected derivative thereof), R$^{11}$ is hydrogen, alkyl, perfluoroalkyl, cycloalkyl, cycloalkylalkyl, perfluoroaryl, perfluoroarylakyl or a group selected from aryl and arylalkyl (which group is optionally substituted at its aryl ring with one to two radicals selected from amino, halo, hydroxy, optionally halo-substituted alkyl, alkyloxy, nitro, alkylsulfonyl and arylsulfonyl, or a protected derivative thereof), R$^{12}$ and R$^{13}$ are independently hydrogen, alkyl, cycloalkyl, cycloalkylalkyl, aryl or aralkyl and R$^{14}$ is —C(O)OR$^{10}$, in which R$^{10}$ is as defined above, or a group selected from Formula (a) and (b):

(a)
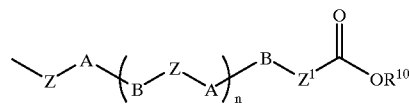

(b)
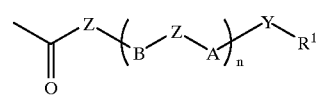

wherein each n, A, B, Y, Z, R$^1$ and R$^{10}$ are as defined above in claim 4; or a pharmaceutically acceptable salt, isomer or mixtureof isomers thereof.

8. The method of claim 7, wherein said cathepsin S inhibitor is a compound, wherein each R$^1$ is 1-piperizinylcarbonyl, 4-methyl-1-piperazinylcarbonyl or 4-morpholinylcarbonyl; R$^8$ is 2-phenylethyl; and R$^7$ is optionally substituted benzyl, 1-naphthylmethyl or 2-naphthylmethyl.

9. The method of claim 8, wherein said cathepsin S inhibitor is a compound, wherein R$^1$ is 4-morpholinylcarbonyl, R$^1$ is 2-phenylethyl, R$^7$ is benzyl and R$^1$ is benzylcarbamoyl namely N$^2$-4-(morpholinylcarbonyl)-N$^1$→3-phenyl-1S-(2-benzylcarbamoylethyl)propyl-L-phenylalaninamide.

10. A method of claim 1, wherein said cathepsin S inhibitor is a compound of formula:

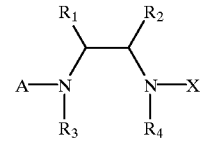

wherein A and X are N-substituents selected from the group consisting of acyl, acyl peptidyl, alkyloxycarbonyl, alkyloxycarbonyl peptidyl, sulfonyl, peptidyl, sulfamoyl, sulfamoyl peptidyl, sulfinyl, sulfinyl peptidyl, carbamoyl, and carbamoyl peptidyl;

R$_1$ is (a) an amino acid side chain or (b) hydrogen;

R$_2$ is (a) an amino acid side chain or (b) hydrogen, wherein either (1) both R$_1$ and R$_2$ are hydrogen, or (2) one of R$_1$ or R$_2$ is an amino acid side chain and the other one of R$_1$ and R$_2$ is hydrogen; and R$_3$ and R$_4$ are hydrogen, or are bonded together to form ethylene or substituted ethylene;

wherein said ethylene substituent is an amino acid side chain.

11. A method of claim 1, wherein said cathepsin S inhibitor is a compound of formula:

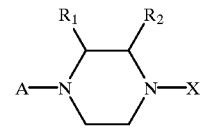

wherein A is a N-substituent selected from the group consisting of acyl peptidyl, alkyloxycarbonyl peptidyl, peptidyl, sulfamoyl peptidyl, sulfinyl peptidyl, and carbamoyl peptidyl; X is a N-substituent selected from the group consisting of acyl, acyl peptidyl, alkyloxycarbonyl, alkyloxycarbonyl peptidyl, sulfonyl, sulfonyl peptidyl, peptidyl, sulfamoyl, sulfamoyl peptidyl, sulfinyl, sulfinyl peptidyl, carbamoyl, and carbamoyl peptidyl;

$R_1$ is hydrogen; and $R_2$ is an amino acid side chain.

12. A method of claim 1, wherein said cathepsin S inhibitor is a compound of formula:

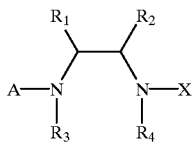

wherein A and X are N-substituents selected from the group consisting of $C(O)R_7$(acyl), acyl peptidyl, $C(O)OR_8$ (alkyloxycarbonyl), alkyloxycarbonyl peptidyl, $S(O)2R_9$ (sulfonyl), peptidyl, $S(O)_2NR_{10}R_{11}$, (sulfamoyl), sulfamoyl peptidyl, $S(O)R_9$(sulfinyl), sulfinyl peptidyl, $C(O)NR_{10}R_{11}$ (carbamoyl), and carbamoyl peptidyl;

$R_7$ is selected from the group consisting of $(C_{1-5})$alkyl, $(C_{3-7})$cycloalkyl, $(C_{3-7})$cycloalkyl$(C_{1-5})$alkyl, $(C_{3-7})$ cycloalkyl$(C_{1-5})$alkenyl, hetero$(C_{3-7})$cycloalkyl, $(C_{5-14})$aryl, substituted$(C_{5-14})$aryl, $(C_{7-12})$aralkyl, and substituted$(C_{7-12})$aralkyl; wherein said hetero group is selected from the group consisting of hydroxy, $(C_{1-5})$ alkyl, hetero$(C_{3-7})$cycloalkyl, $(C_{1-5})$alkanoyl, $(C_{1-5})$ alkoxycarbonyl, $(C_{5-14})$aryl$(C_{1-5})$alkoxycarbonyl, and hetero$(C_{3-7})$cycloalkylcarbonyl;

$R_8$ is selected from the group consisting of $(C_{1-5})$alkyl (optionally substituted with a member of the group consisting of hydroxy, $(C_{1-5})$alkoxy, amino, and halogens of atomic number 9-35), $(C_{3-7})$cycloalkyl, $(C_{3-7})$ cycloalkyl$(C_{1-5})$alkyl, $(C_{3-7})$cycloalkyl$(C_{1-5})$alkenyl, $(C_{5-14})$aryl, substituted$(C_{5-14})$aryl, $(C_{7-12})$aralkyl, and substituted$(C_{7-12})$aralkyl;

$R_9$ is selected from the group consisting of $(C_{1-5})$alkyl (optionally substituted with a member of the group consisting of hydroxy, $(C_{1-5})$alkoxy, amino, and halogens of atomic number 9-35), $(C_{3-7})$cycloalkyl, $(C_{3-7})$ cycloalkyl$(C_{1-5})$alkyl, $(C_{3-7})$cycloalkyl$(C_{1-5})$alkenyl, $(C_{5-14})$aryl, substituted$(C_{5-14})$aryl, $(C_{7-12})$aralkyl, and substituted$(C_{7-12})$aralkyl;

$R_{10}$ and $R_{11}$ are independently selected from the group consisting of hydrogen, $(C_{1-5})$alkyl, $(C_{3-7})$cycloalkyl, $(C_{3-7})$cycloalkyl$(C_{1-5})$alkyl, $(C_{5-14})$aryl, substituted $(C_{5-14})$aryl, $(C_{7-12})$aralkyl, substituted$(C_{7-12})$aralkyl; di$(C_{1-5})$alkyl, $(C_{1-5})$alkyl$(C_{5-12})$aralkyl; or $R_{10}$ and $R_{11}$ are bonded to form a 5 or 6 membered alicyclic or heteroalicylic ring moieties;

Peptidyl is 1–10 amino acids;

said substituents of said substituted aryl and substituted aralkyl are 1 or 2 members of the group consisting of $(C_{1-5})$alkyl, $(C_{1-5})$alkoxy, halogens of atomic number 9-35, hydroxy, and amino;

$R_1$ is (a) an amino acid side chain or (b) hydrogen;

$R_2$ is (a) an amino acid side chain or (b) hydrogen, wherein either (1) both R, and $R_2$ are hydrogen, or (2) one of $R_1$ or $R_2$ is an amino acid side chain and the other one of $R_1$ and $R_2$ is hydrogen; and $R_3$ and $R_4$ are hydrogen, or are bonded together to form ethylene or substituted ethylene wherein said ethylene substituent is an amino acid side chain.

13. A method of claim 1, wherein said cathepsin S inhibitor is a compound of formula:

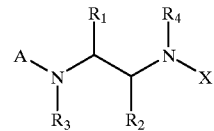

wherein A and X are independently $R_{13}$—$X_1$—;

$R_{13}$ is selected from the group consisting of hydrogen, alkyloxycarbonylalkanoyl of overall 3–10 carbon atoms, $(C_{1-9})$alkyloxycarbonyl, $(C_{2-10})$alkanoyl (optionally substituted with a radical selected from carboxy, $(C_{1-9})$alkyloxycarbonyl and hetero$(C_{4-8})$ cycloalkyl$(C_{2-10})$alkanoylamino), $(C_{4-8})$ cycloalkylcarbonyl, hetero$(C_{4-8})$cycloalkylcarbonyl (optionally substituted with a radical selected from hydroxy, $(C_{1-5})$alkyl, hetero$(C_{4-8})$cycloalkyl, $(C_{1-5})$ alkanoyl, $(C_{1-5})$alkyloxycarbonyl, $(C_{6-10})$aryl$(C_{1-5})$ alkyloxycarbonyl and hetero$(C_{4-8})$cycloalkylcarbonyl), $(C_{6-10})$aryl$(C_{1-5})$alkyloxycarbonyl, carbamoyl, $(C_{1-5})$ alkylcarbamoyl, di$(C_{1-5})$alkylcarbamoyl, $(C_{6-10})$ arylcarbamoyl, $(C_{6-10})$aryl$(C_{1-5})$alkylcarbamoyl, $(C_{6-10})$aryl$(C_{1-5})$alkanoyl, $(C_{7-11})$aroyl, $(C_{1-10})$ alkylsulfonyl, $(C_{6-10})$arylsulfonyl, $(C_{6-10})$aryl$(C_{1-5})$ alkylsulfonyl, $(C_{1-5})$alkylsulfamoyl, di$(C_{1-5})$ alkylsulfamoyl, $(C_{6-10})$arylsulfamoyl, $(C_{1-5})$ alkylsulfinyl, di$(C_{1-5})$alkylaminosulfinyl, and $(C_{6-10})$ arylsulfinyl;

$X_1$ is a bond or a divalent radical of formula (a) or (b):

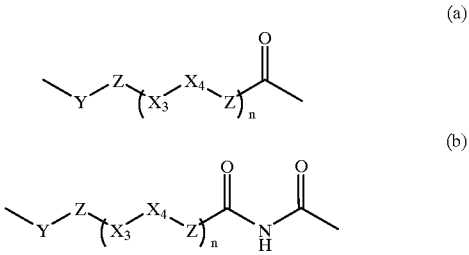

n is 0 to 9; $X_3$–$X_4$ represents a linkage selected from —C(O)NR$_{14}$—, —CH$_2$NR$_{14}$—, —C(O)CH$_2$— and —NR$_{14}$C(O)—;

Y is —CH(R$_{14}$) or —NR$_{14}$—;

Z is —(CH$_2$)$_{2'}$, —C(R$_{15}$)(R$_{16}$)— or —N(R$_{16}$)—;

$R_{14}$ is hydrogen or as defined below;

$R_{15}$ is hydrogen or methyl;

each $R_{16}$ is independently hydrogen, $(C_{1-5})$alkyl (optionally substituted with a radical selected from hydroxy, $(C_{1-5})$alkyloxy, amino, $(C_{1-5})$alkylamino, di$(C_{1-5})$alkylamino, uriedo, $(C_{1-5})$ alkyluriedo, mercapto, $(C_{1-5})$alkylthio, carboxy, carbamoyl, $(C_{1-5})$ alkylcarbamoyl, di$(C_{1-5})$alkylcarbamoyl, $(C_{1-5})$ alkylsulfinyl, $(C_{1-5})$alkylsulfonyl, guanidino, —P(O) (OR$_{12}$)$_2$, —OP(O)(OR$_{12}$)$_2$ or —OP(O)(R$_{12}$)$_2$, $(C_{3-7})$ cycloalkyl, $(C_{3-7})$cycloalkyl$(C_{1-5})$alkyl, $(C_{5-14})$aryl, $(C_{5-14})$aryl$(C_{1-5})$alkyl (which group is optionally substituted at its aryl ring with one to three radicals selected from hydroxy, amino, guanidino, a halogen, optionally halogen substituted $(C_{1-5})$alkyl, $(C_{1-5})$ alkyloxy and $(C_{5-4})$aryl, or a protected derivative thereof) or together with an adjacent $R_{14}$ forms a divalent radical selected from $(C_{3-4})$methylene and 1,2-phenylenedimethylene (which radical is optionally substituted with hydroxy, or a protected derivative thereof, or oxo), with the proviso X and A are not both hydrogen;

each $R_{12}$ is independently hydrogen or $(C_{1-5})$alkyl or a protected derivative thereof;

$R_1$ and $R_2$ are both hydrogen or one of $R_1$ or $R_2$ is cyano, carboxy, $(C_{1-5})$alkyloxycarbonyl, $(C_{1-5})$alkanoyl, carbamoyl, $(C_{1-5})$alkylcarbamoyl, di$(C_{1-5})$alkylcarbamoyl, $(C_{1-5})$alkyloxy($(C_{1-5})$alkyl)carbamoyl, amino$(C_{1-5})$alkylcarbamoyl, $R_{16}$, as defined above, or $R_{13}$—$X_2$—, wherein $R_{13}$ is as defined above and $X_2$ is a divalent radical of formulae (a) or (b), as defined above;

$R_3$ and $R_4$ are hydrogen or together form optionally substituted ethylene, wherein said ethylene substituent is an amino acid side chain or are independently $R_{14}$, as defined above; or a pharmaceutically acceptable salt, isomer or mixture of isomers thereof.

14. A method of claim 1, wherein said CatS inhibitor is a compound of formula:

$$R\text{—}[L]_x\text{—}X_1\text{—}\underset{\underset{R_2}{H}}{N}\text{—}\underset{\underset{Y}{\overset{R_3}{|}}}{C}\text{—}\underset{\underset{R_5}{H}}{N}\text{—}\underset{\underset{}{\overset{R_4}{|}}}{C}\text{—}C\equiv N$$

wherein:

R is optionally substituted (aryl, lower alkyl, lower alkenyl, lower alkynyl, or heterocyclyl); $R_2$ and $R_3$ are independently hydrogen, or optionally substituted; or $R_2$ and $R_3$ together represent lower alkylene, optionally interrupted by O, S or $NR_6$, so as to form a ring with the carbon atom to which they are attached wherein R is hydrogen, lower alkyl or aryl-lower alkyl; or either $R_2$ or $R_3$ are linked by lower alkylene to the adjacent nitrogent to form a ring; $R_4$ and $R_5$ are independently H, or optionally substituted (lower alkyl, aryl-lower alkyl), $C(O)OR_7$, or —C(O)$NR_7R_8$, wherein $R_7$is optionally substituted (lower alkyl, aryl, aryl-lower alkyl, cycloalkyl, bicycloalkyl or heterocyclyl), and $R_8$ is H, or optionally substituted (lower alkyl, aryl, aryl-lower alkyl, cycloalkyl, bicycloalkyl or heterocyclyl), or $R_4$ and $R_5$ together represent lower alkylene, optionally interrupted by O, S or $NR_6$ so as to form a ring with the carbon atom to which they are attached wherein $R_6$ is hydrogen, lower alkyl or aryl-lower alkyl, or $R_4$is H or optionally substituted lower alkyl and $R_5$ is a substituent of formula —$X_2$—$(Y_1)_n$—$(Ar)_p$—Q—Z wherein $Y_1$ is O, S, SO, $SO_2$, $N(R_6)SO_2$, N—R6, $SO_2NR_6$, $CONR_6$ or $NR_6CO$;

n is zero or one;

p is zero or one;

$X_2$ is lower alkylene; or when n is zero, $X_2$ is also $C_2$–$C_7$-alkylene interrupted by O, S, SO, $SO_2$, $NR_6$, $SO_2NR_6$, $CONR_6$ or $NR_6CO$;

wherein $R_6$ is hydrogen, lower alkyl or aryl-lower alkyl;

Ar is arylene;

Z is hydroxy, acyloxy, carboxyl, esterified carboxyl, amidated carboxyl, aminosulfonyl, (lower alkyl or aryl-lower alkyl)aminosulfonyl, or (lower alkyl or aryl-lower alkyl)sulfonylaminocarbonyl; or Z is tetrazolyl, triazolyl or imidazolyl; Q is direct bond, lower alkylene, $Y_1$-lower alkylene or $C_2$–$C_7$-alkylene interrupted by $Y_1$;

$X_1$ is —C(O)—, —C(S)—, —S(O)—, —S(O)$_2$—, or —P(O)(OR$_6$)—, wherein $R_6$ is as defined above;

Y is oxygen or sulfur;

L is optionally substituted —Het—, —Het—$CH_2$— or —$CH_2$—Het—, wherein Het is a hetero atom selected from O, N or S, and x is zero or one;

and aryl in the above definitions represents carboxylic or heterocyclic aryl; or a physiologically-acceptable and -cleavable ester or a salt thereof.

15. A method of claim 14, provided that when R is lower alkyl not substituted by aryl, one of $R_4$ or $R_5$ is a substituent of formula —$X_2$—$(Y_1)_n$—$(Ar)_p$—Q—Z;

provided that when x is one, L is —O—, or —$CH_2$—O— and $X_1$ is —C(O)—, either one of $R_4$ or $R_5$ is a substituent of formula —$X_2$—$(Y_1)_n$—$(Ar)_p$—Q—Z, or R is not unsubstituted phenyl;

provided that when $R_2$=$R_4$=$R_5$=H, x is zero and $X_1$ is —C(O)—, $R_3$ is not H, —$CH_3$, —CH($CH_3$)$_2$, —$CH_2$—CH—($CH_3$)$_2$, —$CH_2$—COOH, or —$CH_2$—COO—$CH_2$—$CH_3$, when R is unsubstituted phenyl, $R_3$ is not H, —CH($CH_3$)$_2$, or —$CH_2$—CH—($CH_3$)$_2$, when R is 4-aminophenyl or 4-nitrophenyl, $R_3$ is not H when R is 3-aminophenyl, 3-nitrophenyl 2-chloropyridin-4-yl, or vinyl or $R_3$ is not —$CH_2$—$CH_2$—S—$CH_3$ when R is pyridin-3-yl or 2-chloropyridin-4-yl, provided that when $R_2$=$R_3$=$R_4$=H, x is zero and $X_1$ is —C(O)— and R is phenyl, $R_5$ is not —CH($CH_3$)$_2$, provided that when $R_3$=$R_4$=H, $R_5$ is —$CH_2$—$CH_2$—COOH, x is zero and $X_1$ is —C(O)—, $R_2$ does not form a heterocyclic ring with the adjacent nitrogen atom, and provided that when $R_2$=$R_3$=$R_4$=$R_5$=H, x is zero and $X_1$ is —$SO_2$—, R is not 4-methylphenyl.

16. A method of claim 1, wherein said CatS inhibitor is a compound of formula III $$R_{30}\text{—}\underset{H}{N}\text{—}\underset{\underset{R_{33}}{\overset{R_{32}}{|}}}{C}\text{—}CONH\text{—}\underset{\underset{X_2\text{—}(Y_1)_n\text{—}(Ar)_p\text{—}Q\text{—}Z}{\overset{R_{34}}{|}}}{C}\text{—}C\equiv N$$

wherein $R_{30}$ is an acyl group derived from an organic carboxylic, carbonic, carbamic or sulfonic acid; $R_{32}$ and $R_{33}$ are independently hydrogen, lower alkyl, cycloalkyl, bicycloalkyl, or (aryl, biaryl, cycloalkyl or bicycloalkyl)-lower alkyl; or $R_{32}$ and $R_{33}$ together represent lower alkylene so as to form a ring together with the carbon to which they are attached;

$R_{34}$ is hydrogen or lower alkyl;

$X_2$, $Y_1$, Ar, Q, Z, n and p are as defined in claim 14; or a pharmaceutically acceptable salt or ester thereof.

17. A method of claim 16, wherein said CatS inhibitor is compound wherein (a) p is one;

(b) Y1 is O, S, SO, $SO_2$, $N(R_6)SO_2$ or N—$R_6$; and (c) $X_2$ is lower alkylene; or when n is zero, $X_2$ is also $C_2$–$C_7$-alkylene interrupted by O, S, SO, $SO_2$ or $NR_6$, (d) $R_{30}$ is an acyl group derived from an organic carboxylic, carbamic, or sulfonic acid, (e) and pharmaceutically acceptable salts and esters thereof.

18. A method of claim 14, wherein said CatS inhibitor is a compound of the formula:

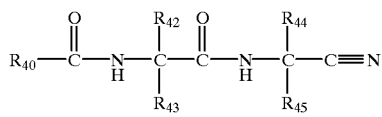

wherein $R_{40}$ is substituted phenyl or heterocyclic aryl, (mono- or di-carbocyclic or heterocyclic aryl)-lower alkyl or lower alkenyl, or heterocyclyl;

$R_{42}$ is hydrogen or lower alkyl;

$R_{43}$ is carbocyclic or heterocyclic aryl or lower alkyl;

$R_{44}$ and $R_{45}$ are independently hydrogen or lower alkyl; or $R_{44}$ and $R_{45}$ combined represent lower alkylene;

Or a pharmaceutically acceptable salt or ester thereof.

* * * * *

UNITED STATES PATENT AND TRADEMARK OFFICE
CERTIFICATE OF CORRECTION

PATENT NO. : 6,369,032 B1  
DATED : April 9, 2002  
INVENTOR(S) : Yin Gu et al.

It is certified that error appears in the above-identified patent and that said Letters Patent is hereby corrected as shown below:

Title page,  
Item [56], References Cited, U.S. PATENT DOCUMENTS, add,  
-- 5,976,858 * 11/1999 Palmer et al...435/219 --  
OTHER PUBLICATIONS, "Palmer,..." reference, "e al.;" should read -- et al. --; "Chapman, H.A." reference, "Poteolysis" should read -- Proteolysis --; and "curr." should read -- Curr. --; "Nakagawa, T.Y. et al.;" reference, "datiion" should read -- dation --; and "Shi, Guo-Ping, et al.;" reference, "Norman" should read -- Normal --.

Column 18,  
Line 6, "$R_6$" should read -- $R^6$ --.

Column 20,  
Line 9, "$Z^1$" should read -- Z --.  
Line 18, "mixtureof" should read -- mixture of --.

Column 23,  
Line 32, "substituted, or" should read -- substituted (lower alkyl, cycloalkyl, bicycloalkyl, or (aryl, biaryl, cycloalkyl or bicycloalkyl)-lower alkyl); or --.  
Line 44, "$R_7$is" should read -- $R_7$ is --.  
Line 58, "N-R6," should read -- $N-R_6$ --.

Column 25,  
Line 2, "Y1" should read -- $Y_1$ --.

Signed and Sealed this

Second Day of December, 2003

JAMES E. ROGAN  
*Director of the United States Patent and Trademark Office*